United States Patent
Ohta et al.

(10) Patent No.: US 8,697,912 B2
(45) Date of Patent: Apr. 15, 2014

(54) N-(1-HYDROXYETHYL) CARBOXAMIDE COMPOUND AND PROCESS FOR PRODUCING SAME

(75) Inventors: Keisuke Ohta, Tokyo (JP); Syunichi Nagamatsu, Tokyo (JP); Tetsuya Ishii, Tokyo (JP)

(73) Assignee: Showa Denko K.K., Tokyo (JP)

( * ) Notice: Subject to any disclaimer, the term of this patent is extended or adjusted under 35 U.S.C. 154(b) by 63 days.

(21) Appl. No.: 13/143,426
(22) PCT Filed: Jan. 5, 2010
(86) PCT No.: PCT/JP2010/050015
§ 371 (c)(1),
(2), (4) Date: Aug. 22, 2011
(87) PCT Pub. No.: WO2010/079774
PCT Pub. Date: Jul. 15, 2010

(65) Prior Publication Data
US 2011/0294974 A1 Dec. 1, 2011

(30) Foreign Application Priority Data
Jan. 6, 2009 (JP) .................. 2009-000542

(51) Int. Cl.
C07C 225/02 (2006.01)
C07C 225/06 (2006.01)
(52) U.S. Cl.
USPC ........... 564/215; 564/123; 564/201; 564/203; 564/204; 564/224; 526/303.1
(58) Field of Classification Search
USPC ............... 526/303.1; 564/215, 123, 201, 203, 564/204, 224
See application file for complete search history.

(56) References Cited

U.S. PATENT DOCUMENTS 3,526,620 A * 9/1970 Bestian et al. ............... 540/451
4,837,337 A * 6/1989 Murao et al. ................. 548/551

(Continued)

FOREIGN PATENT DOCUMENTS

EP    1 400 858 A1    3/2004
JP    61-036249 A    2/1986

(Continued)

OTHER PUBLICATIONS

International Preliminary Report on Patentability issued on Aug. 25, 2011 for counterpart application PCT/JP2010/050015.

(Continued)

Primary Examiner — Ling Choi
Assistant Examiner — David L Miller
(74) Attorney, Agent, or Firm — Sughrue Mion, PLLC

(57) ABSTRACT

The present invention relates to an N-(1-hydroxyethyl)carboxamide compound represented by formula (1)

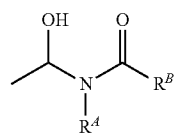

(1)

(in the formula, $R^A$ and $R^B$ represent independently from each other a hydrogen atom or an alkyl group having 1 to 4 carbon atoms except for a case where $R^A$ and $R^B$ represent a hydrogen atom at the same time) and a method for producing the same; a method for producing an N-(1-alkoxyethyl)carboxamide compound; a method for producing an N-vinyl carboxylic acid amide compound; and a method for producing an N-vinyl carboxylic acid amide (co)polymer. An N-(1-alkoxyethyl)carboxamide compound can be obtained by reacting N-(1-hydroxyethyl)carboxamide compound with alcohol in the presence of an acid catalyst, and an N-vinyl carboxylic acid amide compound, which is a monomer of the N-vinyl carboxylic acid amide (co)polymer, can be obtained by thermally decomposing or catalytically decomposing the N-(1-alkoxyethyl)carboxamide compound.

2 Claims, 2 Drawing Sheets

(56) References Cited

U.S. PATENT DOCUMENTS

| | | | |
|---|---|---|---|
| 5,527,963 A | * | 6/1996 | Sato et al. ............ 564/215 |
| 5,574,185 A | * | 11/1996 | Sato et al. ............ 564/224 |
| 6,107,336 A | * | 8/2000 | Elbe et al. ............ 514/471 |
| 2004/0081922 A1 | * | 4/2004 | Ikemoto et al. ........ 430/329 |

FOREIGN PATENT DOCUMENTS

| | | | |
|---|---|---|---|
| JP | 6-100515 A | | 4/1994 |
| JP | 6-298713 A | | 10/1994 |
| JP | 06298713 A | * | 10/1994 |
| JP | 10-130216 A | | 5/1998 |
| WO | WO 2007/018279 A1 | | 2/2007 |

OTHER PUBLICATIONS

European Search Report issued Feb. 22, 2012 in European Patent Application No. 10729194.

Giada Amato, et al., "Microsomal Oxidation of N, N-Diethylformamide and Its Effect on P450-Dependent Monooxygenases in Rat Liver", Chemical Research in Toxicology, vol. 9, No. 5, pp. 882-890 (Jan. 1, 1996).

Geng, Bolin, et al., "Exploring 9-benzyl purines as inhibitors of glutamate racemase (MurI) in Gram-positive bacteria," Bioorganic & Medicinal Chemistry Letters, 2008, pp. 4368-4372, vol. 18, No. 15.

Kiren, Sezgin, et al., "Direct carbinolamide synthesis." Tetrahedron Letters, 2007, pp. 7456-7459, vol. 48, No. 42.

* cited by examiner

N-(1-HYDROXYETHYL) CARBOXAMIDE COMPOUND AND PROCESS FOR PRODUCING SAME

CROSS REFERENCE TO RELATED APPLICATIONS

This application is a National Stage of International Application No. PCT/JP2010/050015 filed Jan. 5, 2010, claiming priority based on Japanese Patent Application No. 2009-000542, filed Jan. 6, 2009, the contents of all of which are incorporated herein by reference in their entirety.

TECHNICAL FIELD

The present invention relates to N-(1-hydroxyethyl)carboxamide compound and a method for producing the same, a method for producing N-vinylcarboxamide compound using N-(1-hydroxyethyl)carboxamide compound as a starting material, a method for producing N-(1-alkoxyethyl)carboxamide compound as being a precursor of N-vinyl carboxylic acid amide compound, and a method for producing a (co)polymer of N-vinyl carboxylic acid amide.

BACKGROUND ART

N-(1-hydroxyethyl)carboxamide is useful as an intermediate material to synthesize N-(1-alkoxyethyl)carboxamide as being a precursor of N-vinyl carboxylic acid amide.

As a method for producing N-vinylformamide, JP-A-H06-298713 (Patent Document 1) teaches that N-vinylformamide can be produced by thermal decomposition of N-(1-methoxyethyl)formamide produced via N-(1-hydroxyethyl)formamide. However, the publication has no mention on other N-(1-hydroxyethyl)carboxamide or on a method for producing N-vinyl carboxylic acid amide produced via other N-(1-hydroxyethyl)carboxamide.

On the other hand, JP-A-H06-100515 (Patent Document 2) discloses a method for producing N-(α-alkoxyethyl)-carboxamide as being a precursor of N-vinyl carboxylic acid amide from carboxylic amide, alcohol, acetal and the like in the presence of an acid catalyst. This production method is excellent in that the materials are easily available and that N-(α-alkoxyethyl)-carboxamide can be produced in one step without producing N-(1-hydroxyethyl)carboxamide. However, this method requires alcohol and acetal in large excess to carboxylic acid amide; and needs to recover alcohol and acetal from the reaction solution containing N-(α-alkoxyethyl)-carboxamide for recycling, and therefore the method is suitable for mass production but not necessarily suitable for the production in small lots in multipurpose plants.

PRIOR ART

Patent Documents

Patent Document 1: JP-A-H06-298713
Patent Document 2: JP-A-H06-100515

DISCLOSURE OF THE INVENTION

Problems to be Solved by the Invention

An objective of the present invention is to provide a novel N-(1-hydroxyethyl)carboxamide compound and a production method thereof, a method for producing N-(1-alkoxyethyl)carboxamide compound, a method for producing N-vinyl carboxylic acid amide compound, and a method for producing (co)polymer of N-vinyl carboxylic acid amide.

Means to Solve the Problem

As a result of intensive studies to solve the above problems, the present inventors have found that N-(1-hydroxyethyl)carboxamide compound as a target compound can be obtained by reacting carboxylic acid amide and acetaldehyde in the presence of a basic catalyst, and have accomplished the present invention.

That is, the present invention relates the following [1] to [9].

[1] An N-(1-hydroxyethyl)carboxamide compound represented by formula (1)

[Chem. 1]

(1)

(in the formula, $R^A$ and $R^B$ represent independently from each other a hydrogen atom or an alkyl group having 1 to 4 carbon atoms except for a case where $R^A$ and $R^B$ represent a hydrogen atom at the same time).

[2] The N-(1-hydroxyethyl)carboxamide compound as described in [1] above, where the compound is
N-(1-hydroxyethyl)-N-methylformamide,
N-(1-hydroxyethyl)-N-ethylformamide,
N-(1-hydroxyethyl)acetamide,
N-(1-hydroxyethyl)-N-methylacetamide or
N-(1-hydroxyethyl)-N-ethylacetamide.

[3] A method for producing the N-(1-hydroxyethyl)carboxamide compound represented by formula (1)

[Chem. 3]

(1)

(symbols in the formula have the same meanings as described in [1] above), comprising reacting acetaldehyde and carboxylic acid amide represented by formula (2)

[Chem. 2]

(2)

(symbols in the formula have the same meanings as mentioned above) in the presence of a base.

[4] The method for producing the N-(1-hydroxyethyl)carboxamide compound as described in [3] above, wherein the base is bicarbonate.

[5] The method for producing the N-(1-hydroxyethyl)carboxamide compound as described in [3] or [4] above, wherein the reaction is carried out in methylcyclohexane.

[6] The method for producing the N-(1-hydroxyethyl)carboxamide compound as described in [3] or [4] above, wherein the reaction is carried out in the presence of an N-(1-hydroxyethyl)carboxamide compound.

[7] A method for producing the N-(1-alkoxyethyl) carboxamide compound represented by formula (3)

[Chem. 6]

(3)

(In the formula, $R^A$ and $R^B$ have the same meanings as described in [1] above and $R^C$ represents an alkyl group having 1 to 4 carbon atoms) comprising reacting N-(1-hydroxyethyl)carboxamide compound represented by formula (1)

[Chem. 4]

(1)

(symbols in the formula have the same meaning as mentioned above) and alcohol represented by formula (4)

[Chem. 5]

$R^C OH$ (4)

(in the formula, $R^C$ represents an alkyl group having 1 to 4 carbon atoms) in the presence of an acid catalyst.

[8] A method for producing the N-vinyl carboxylic acid amide compound represented by formula (5)

[Chem. 10]

(5)

(symbols in the formula have the same meanings as described in [1] above) through thermal decomposition or catalytic cracking of N-(1-alkoxyethyl)carboxamide compound represented by formula (3)

[Chem. 9]

(3)

(in the formula, $R^A$ and $R^B$ have the same meanings as described in [1] above and $R^C$ has the same meaning as described in [7] above) obtained by reacting N-(1-hydroxyethyl)carboxamide compound represented by formula (1)

[Chem. 7]

(1)

(symbols in the formula have the same meanings as mentioned above) and alcohol represented by formula (4)

[Chem. 8]

$R^C OH$ (4)

(symbols in the formula have the same meanings as mentioned above) in the presence of an acid catalyst.

[9] A method for producing a (co)polymer of N-vinyl carboxylic acid amide, comprising obtaining an N-vinyl carboxylic acid amide compound represented by formula (5)

[Chem. 14]

(5)

(symbols in the formula have the same meanings as described in [1] above) through thermal decomposition or catalytic cracking of N-(1-alkoxyethyl)carboxamide compound represented by formula (3)

[Chem. 13]

(3)

(in the formula, $R^C$ has the same meaning as described in [7] above and $R^A$ and $R^B$ have the same meanings as mentioned above) obtained by reacting N-(1-hydroxyethyl)carboxamide compound represented by formula (1)

[Chem. 11]

(1)

(symbols in the formula have the same meanings as mentioned above) and alcohol represented by formula (4)

[Chem. 12]

$R^C OH$ (4)

(symbols in the formula have the same meanings as mentioned above) in the presence of an acid catalyst; and homopolymerization of the N-vinyl carboxylic acid amide compound or copolymerization of the compound with other monomers which can be copolymerized.

Effects of the Invention

The N-(1-hydroxyethyl)carboxamide compound obtained by the present invention is useful as an intermediate material for synthesizing an N-vinyl carboxylic acid amide compound.

Since the N-vinyl carboxylic acid amide compound according to the production method of the present invention using N-(1-hydroxyethyl)carboxamide as a starting material contains a polymerization-inhibiting substance moderately compared to the conventionally produced N-vinyl carboxylic acid amide compound, the method can provide an excellent polymerizable monomer being well-balanced in polymerizability and preservation stability.

MODE FOR CARRY OUT THE INVENTION

The present invention will be described in more details hereinafter.

In the present invention, an N-(1-hydroxyethyl)carboxamide compound refers to N-(1-hydroxyethyl)-N-alkylformamide and N-(1-hydroxyethyl)carboxylic acid amide, and an N-(1-alkoxyethyl)carboxylic acid amide compound refers to N-(1-alkoxyethyl)-N-alkylformamide and N-(1-alkoxyethyl)carboxylic acid amide. Also, an N-vinyl carboxylic acid amide compound refers to N-vinyl alkylformamide and N-vinyl carboxylic acid amide, and an N-vinyl carboxylic acid amide polymer refers to poly-N-vinylalkylformamide and poly-N-vinyl carboxylic acid amide. N-vinyl carboxylic acid amide (co)polymer refers to a polymer of the above-mentioned N-vinyl carboxylic acid amide and/or a copolymer of N-vinyl carboxylic acid amide, and a copolymer of N-vinyl carboxylic acid amide is a copolymer of N-vinyl carboxylic acid amide and a monomer other than N-vinyl carboxylic acid amide.

Also, an N-1,3-butadienyl carboxylic acid amide compound refers to N-1,3-butadienyl-N-alkylformamide and N-1,3-butadienyl carboxylic acid amide.

N-(1-hydroxyethyl)carboxylic Acid Amide Compound

The N-(1-hydroxyethyl)carboxylic acid amide compound of the present invention is represented by formula (1).

[Chem. 15]

(1)

In the formula, $R^A$ and $R^B$ represent independently from each other a hydrogen atom or an alkyl group having 1 to 4 carbon atoms except for a case where $R^A$ and $R^B$ represent a hydrogen atom at the same time.

Specific examples of the alkyl group having 1 to 4 carbon atoms represented by $R^A$ and $R^B$ include methyl group, ethyl group, n-propyl group, i-propyl group, n-butyl group, i-butyl group, s-butyl group and t-butyl group.

There is no particular limitation on the type of the alkyl group having 1 to 4 carbon atoms represented by $R^A$ and $R^B$, and the type can be freely selected. When an alkyl group having a smaller number of carbon atoms is used, an N-(1-hydroxyethyl)-N-alkyl carboxylic acid amide compound and an N-vinyl-N-alkyl carboxylic acid amide compound derived thereof tend to have higher hydrophilicity compared to the compound using an alkyl group having a larger number of carbon atoms. Accordingly, the type of an alkyl group can be freely selected depending on the desired hydrophilicity.

Specific examples of N-(1-hydroxyethyl) carboxylic acid amide compound includes N-(1-hydroxyethyl)-N-methylformamide, N-(1-hydroxyethyl)-N-ethylformamide, N-(1-hydroxyethyl)acetamide, N-(1-hydroxyethyl)-N-methylacetamide and N-(1-hydroxyethyl)-N-ethylacetamide.

Method for Producing an N-(1-hydroxyethyl)carboxylic Acid Amide Compound

N-(1-hydroxyethyl)carboxylic acid amide compound of the present invention can be produced by reacting acetaldehyde and an amide compound.

An amide compound as a raw material in the present invention is carboxylic acid amide represented by formula (2).

[Chem. 16]

(2)

$R^A$ and $R^B$ in the formula have the same meanings as mentioned above.

Specific examples of carboxylic acid amide represented by formula (2) include N-methylformamide, N-ethylformamide, N-(n-propyl)formamide, N-(i-propyl)formamide, N-(n-butyl)formamide, N-(s-butyl)formamide, N-(i-butyl)formamide, N-(t-butyl)formamide, acetamide and N-alkyl derivative thereof; propionamide and N-alkyl derivative thereof; butanamide and N-alkyl derivative thereof; 2-methylpropionamide and N-alkyl derivative thereof; pentanamide and N-alkyl derivative thereof; 3-methylbutanamide and N-alkyl derivative thereof; 2-methylbutanamide and N-alkyl derivative thereof; and 2,2-dimethylpropionamide and N-alkyl derivative thereof. Examples of N-alkyl group include alkyl group having 1 to 4 carbon atoms: e.g. methyl group, ethyl group, n-propyl group, i-propyl group, n-butyl group, i-butyl group, s-butyl group and t-butyl group.

The reaction of acetaldehyde and carboxylic acid amide in the present invention is carried out in the presence of abase catalyst. Examples of the type of a base include an inorganic base such as lithium hydroxide, sodium hydroxide, potassium hydroxide, cesium hydroxide, sodium carbonate, potassium carbonate, cesium carbonate, sodium hydrogen carbonate, potassium hydrogen carbonate, cesium hydrogen carbonate, sodium phosphate, potassium phosphate; sodium hydrogenphosphate, potassium hydrogenphosphate, sodium pyrophosphate and potassium pyrophosphate; organic amines such as triethyl amine, pyridine and morpholine; and ion-exchange resin.

These catalyst may be used solely or in combination of two or more thereof.

Among these bases, bicarbonates, hydrogenphosphates and dihydrogenphosphates are preferable on the point that they can suppress aldol condensation as being a side reaction of acetaldehyde, and bicarbonates are particularly preferable. As an alkali metal ion contained in these bases, potassium ion is preferable in terms of the solubility in an organic solvent. Potassium hydrogen carbonate is most preferable.

The amount of the catalyst to be used is 0.01 to 20 mol %, preferably 0.1 to 10 mol %, and still more preferably 0.2 to 5 mol % to the amount of amide. When the amount of the catalyst to be used is less than 0.01 mol %, it may have a retarding effect on the reaction, and when the amount of the catalyst exceeds 20 mol %, it is economically undesirable.

The amount of the acetaldehyde is 1 to 10 mol, preferably 1 to 6 mol, and still more preferably 1 to 3 mol to 1 mol of the amide compound. When the amount of the acetaldehyde exceeds 10 mol, it is economically undesirable because unreacted acetaldehyde remains in large quantity. When the amount of the acetaldehyde is less than 1 mol, it is undesirable because the unreacted amide compound remains.

The reaction may be carried out without using or using a solvent. Examples of the solvent include aliphatic hydrocarbon such as hexane, heptane, cyclohexane, methylcyclohexane and decaline; aromatic hydrocarbon such as benzene, toluene and xylene; ethers such as dimethoxyethane, diethylene glycol dimethyl ether, tetrahydrofuran, and 1,4-dioxane; esters such as ethyl acetate and butyl acetate; ketones such as acetone and methyl ethyl ketone; amides such as N,N-dimethylformamide and N,N-dimethylacetamide; halogenated hydrocarbon such as chloroform and methylene chloride; and acetonitrile. Among these, methylcyclohexane is particularly preferable in terms of the reaction rate and in having a boiling point which is easy to handle in a factory legislatively from an industrial viewpoint.

When these solvents are used, the solvent may be used solely or in combination of two or more thereof. The amount of the solvent to be used is a mass 0.05 to 20 times, preferably 0.1 to 10 times and more preferably 0.2 to 5 times that of the amide compound.

In the method for producing an N-(1-hydroxyethyl)carboxamide compound of the present invention, the reaction rate can be accelerated by adding in advance N-(1-hydroxyethyl)carboxamide compound as a target compound to a reaction solvent to be reacted. This is attributable to the increase in the affinity of the catalyst and acetamide to the surface of the amide compound, which has low solubility.

The reaction temperature is −10 to 80° C., preferably −5 to 70° C., and more preferably 0 to 60° C. When the temperature is lower than −10° C., it may have a retarding effect on the reaction, while when the reaction exceeds 80° C., acetaldehyde is ready to evaporate from the reaction mixture and be lost due to its low boiling point, which may have a retarding effect on the reaction and is economically undesirable.

The obtained N-(1-hydroxyethyl)carboxamide compound may or may not be purified to be used in the subsequent step.

As the purification method, a known method can be employed. Specific examples include a recrystallization method, column purification using a filler such as silica gel and alumina, purification by distillation and liquid separation. These methods can be employed solely or in combination of two or more thereof.

Method for producing N-(1-alkoxyethyl)carboxamide compound

An N-(1-alkoxyethyl)carboxamide compound represented by formula (3)

[Chem. 18]

(3)

(in the formula, $R^C$ represents alkyl group having 1 to 4 carbon atoms and $R^a$ and $R^B$ have the same meanings as mentioned above) can be produced by reacting the N-(1-hydroxyethyl)carboxamide compound of the present invention with alcohol represented by formula (4)

[Chem. 17]

$R^COH$ (4)

(in the formula, $R^C$ has the same meaning as mentioned in above) in the presence of an acid catalyst.

The N-(1-hydroxyethyl)carboxamide may be used in this process after being purified, after removing low-boiling-point substances such as acetaldehyde without performing further purification, or in a state of containing low-boiling-point substances such as acetaldehyde.

The reaction of the N-(1-hydroxyethyl)carboxamide compound and alcohol is carried out by adding alcohol and an acid catalyst to the mixture containing an N-(1-hydroxyethyl)carboxamide compound.

Examples of the alcohol used in the reaction include methanol, ethanol, 1-propanol, 2-propanol, n-butanol, isobutanol, sec-butanol and tert-butanol. Among these, methanol is most preferable in being available at a low price, and easy to remove alcohol which is generated at the time of producing N-vinyl carboxylic acid amide by thermal decomposition of a N-(1-alkoxyethyl)carboxylic acid amide compound.

The acid catalyst to be used may be either of a homogenous catalyst or a heterogenous catalyst. Examples of the homogenous catalyst include mineral acid such as hydrochloric acid, sulfuric acid, nitric acid and phosphoric acid; heteropoly acid such as phosphotungstic acid; and organic acid such as methane sulfonic acid and p-toluene sulfonic acid. Furthermore, though it may not necessarily be dissolved uniformly, a salt of strong acid and weak base can also be used. Examples of a salt of strong acid and weak base include ammonium sulfate, ammonium chloride and the like. Examples of a heterogenous catalyst include a gel-type and porous-type acidic ion-exchange resin. Specific examples include "DIAION SK-1B", "Amberlite IR-120B", "Dowex 50W", "Amberlite 200C", "Amberlyst 15" and "Dowex MSC-1" (all are the registered trademark). The amount of the catalyst to be used may be 100 to 1,000 ppm in alcohol in the case of a homogenous catalyst. When the N-(1-hydroxyethyl)carboxamide compound is used without purification, it contains the base used in the production of N-(1-hydroxyethyl)carboxamide compound, and therefore the amount of the acid catalyst is determined taking the contained base into account. When the catalyst exceeds 1,000 ppm, it generates carboxylic acid amide and acetamide through decomposition of the N-(1-hydroxyethyl) carboxamide compound, and these react with each other to thereby generate high-boiling-point by-products such as ethylidene bis carboxylic acid amide in large quantity, which is undesirable.

As a method for adding an acid catalyst, it is desirable to add the catalyst after adding alcohol to the reaction liquid in order to minimize side reaction. In the case of a homogenous catalyst, it is desirable to add the catalyst which has been diluted in advance to the reaction liquid. If an undiluted catalyst such as hydrochloric acid and sulfuric acid is added to the reaction liquid, the reactive substrate which comes into contact with strong hydrochloric acid and sulfuric acid tends to cause side reaction before the catalyst is diffused into a whole reaction liquid, which is undesirable. As a diluting solvent, it is desirable to use a compound which is present in the raw material and a reaction liquid, and which does not readily react with an acid catalyst. Specific examples of the diluting solvent include alcohol such as methanol and ethanol; and acetal such as dimethyl acetal and diethyl acetal. It is desirable to add salts of strong acid and weak base to the reaction liquid from the viewpoint of easy charging. It is also desirable to add a heterogenous catalyst such as an ion-exchange catalyst to the reaction liquid from the viewpoint of easy charging.

In the case of using an ion-exchange catalyst, addition of a homogenous catalyst in a small amount is preferable because it can improve the activity life of the ion-exchange resin. Furthermore, using an ion-exchange catalyst in combination can reduce the usage of the homogenous catalyst compared to the case where a homogenous catalyst is used solely, which results in a reduction of neutral salts generated in the neutralization after the reaction and is preferable.

The reaction temperature is generally 0 to 150° C. and preferably 20 to 80° C. A temperature 0° C. or lower leads to a slow reaction and is not desirable. A temperature of 150° C. or more results in an increase of the impurity generation and is not desirable. The reaction time varies depending on the catalyst amount used in the reaction, reaction temperature, the types of the raw material compounds and the like, and is generally selected within the range of 0.05 to 10 hours. The reaction time of 0.1 to 5 hours is particularly preferable. With respect to these reaction conditions, the optimum condition varies depending on the type of the alcohol to be used, and therefore it is important to select the reaction temperature and reaction time suitable for each reaction within the above-mentioned range so as to obtain the N-(1-alkoxyethyl)carboxamide compound as a target compound in good yield. The reaction may be performed either under reduced pressure, under ordinary pressure or under pressure. Generally, the reaction is performed under ordinary pressure.

Method for Producing an N-Vinyl Carboxylic Acid Amide Compound and a Polymer Thereof The N-(1-alkoxyethyl)carboxamide compound obtained by the method of the present invention is a precursor (intermediate) for producing an N-vinyl carboxylic acid amide compound, which is mainly used to derive from the compound a homopolymer or copolymer of an N-vinyl carboxylic acid amide compound, as well as to serve as an intermediate of useful chemicals.

(i) Method for Producing N-Vinyl Carboxylic Acid Amide Compound

The N-(1-alkoxyethyl) carboxamide compound represented by formula (3)

[Chem. 19]

(3)

($R^A$, $R^B$ and $R^C$ in the formula have the same meanings as mentioned above) is converted to N-vinyl carboxylic acid amide compound represented by formula (5)

[Chem. 20]

(5)

($R^A$ and $R^B$ in the Formula have the Same Meanings as Mentioned Above) and alcohol ($R^C$OH) by a known method such as thermal decomposition and catalytic cracking. This reaction is conducted in a gas phase or a liquid phase, for example, at a reaction temperature of 60 to 600° C., reaction time of 0.3 second to two hours and reaction pressure of 13.3 Pa to atmospheric pressure. Examples of the catalyst used in the case of catalytic cracking include an alkali metal salt of carboxylic acid (e.g. potassium acetate), an oxide of alkali metal and alkaline earth metal (e.g. magnesium oxide).

An N-(1-alkoxyethyl)carboxamide compound causes hydrolysis or solvolysis in the presence of acid. Accordingly, it is desirable to locate the equipment used for the reaction of the present invention such as production equipment, isolation equipment, a material tank, product containers and a filtrate tank in atmosphere such as nitrogen and dry air. Also, a small amount of desiccant such as magnesium sulfate may be added to the material in order to prevent hydrolysis reaction of N-(1-alkoxyethyl)carboxamide compound.

Upon converting N-(1-alkoxyethyl) carboxamide compound to N-vinyl carboxylic acid amide compound by thermal decomposition or catalytic cracking according to the method of the present invention, an N-1,3-butadienyl carboxylic acid amide compound is generated as a by-product.

An N-1,3-butadienyl carboxylic acid amide compound is a polymerization inhibiting substance of an N-vinyl carboxylic acid amide compound. That is, in order to obtain an N-vinyl carboxylic acid polymer having high molecular weight and to perform a stable polymerization reaction, the removal or chemical conversion of the N-1,3-butadienyl carboxylic acid amide compound is required.

In the present invention, an N-1,3-butadienyl carboxylic acid amide compound can be reduced or removed from an N-vinyl carboxylic acid amide compound. There is no particular limitation on the method for reducing or removing an N-1,3-butadienyl carboxylic acid amide compound from an N-vinyl carboxylic acid amide compound as long as it is a physical method or a chemical converting method which can easily isolate N-1,3-butadienyl carboxylic acid amide compound from an N-vinyl carboxylic acid amide compound. Examples an embodiment of the purification treatment include physical treatment methods such as a precision distillation method of the N-vinyl carboxylic acid amide compound or a solution thereof, a recrystallization method, a pressure crystallization method, and a physical purification treatment method using an absorbent such as activated carbon; and a method of chemically converting N-1,3-butadienyl carboxylic acid amide compound such as a treatment method by Diels-Alder reaction with p-benzoquinone and the like and a treatment method of 1,3-butathenyl group by selective hydrogenation reaction. These methods can be used singly or in combination of two or more of them.

Hereinafter, the method of reducing or removing the N-1, 3-butadienyl carboxylic acid amide compound in the N-vinyl carboxylic acid amide compound is described in more details.

In the method of the present invention, there are no particular limitations on the distillation apparatus in the case of isolation by precision distillation, and a tray column and a packed column having the number of theoretical plates of 1 to 50 are used, and it is desirable to use a distillation column having a low pressure loss and high rectifying efficiency. Examples of such a column include a packed column with structured packings. Since the N-vinyl carboxylic acid amide compound is liable to thermal alteration, it is desirable to perform distillation at as low a temperature as is possible. Thus, distillation is generally performed under reduced pressure of 0.01 to 100 mmHg. Though the precision distillation can be performed either in a continuous way or in a discontinuous way, continuous distillation is preferable from the viewpoint of productivity and operation stability. There are no particular limitations on the reflux ratio and configured depending on the content of the N-1,3-butadienyl carboxylic acid amide compound, type of N-vinyl carboxylic acid amide compound and performance of the distillation column. However, the reflux ratio of about 0.1 to 20 is generally satisfactory, and the ratio is preferably 0.5 to 10.

The N-vinyl carboxylic acid amide compound obtained by the present invention contains traces of butanal and hexanal which is generated by hydrogenation of 3-hydroxybutanal and 5-hydroxy-2-hexenal, which are generated as a by-product upon production of the N-(1-hydroxyethyl)carboxamide compound, during the selective hydrogenation reaction of the above N-1,3-butadienyl carboxylic acid amide compound. The butanal and hexanal content is 0.5 to 5,000 mass ppm, preferably 5 to 1,000 mass ppm and more preferably 10 to 500 mass ppm. These compounds have no adverse effect on the polymerization reaction when the N-vinyl carboxylic acid amide compound is used for a polymerization reaction in the presence of a polymerization initiator. On the other hand, these compounds exert an effect as a polymerization inhibitor when the N-vinyl carboxylic acid amide compound is stored for long periods of time in the absence of a polymerization initiator, and can prevent it from deterioration such as gelation and polymerization.

[Chem. 21]

3-hydroxybutanal 5-hydroxy-2-hexenal butanal hexanal

In the method of the present invention, when the N-1,3-butadienyl carboxylic acid amide compound is isolated through the recrystallization method by cooling the solutions of the N-vinyl carboxylic acid amide compound, the solutions may be cooled directly, or a recrystallization solvent which is not reactive with the N-vinyl carboxylic acid amide compound and has appropriate solubility may be used. Example of such a solvent include aromatic hydrocarbon such as benzene, toluene and xylene; aliphatic hydrocarbon such as pentane, cyclopentane, hexane, cyclohexane, methylcyclohexane and heptane; alcohols such as methanol, ethanol, n-propyl alcohol, isopropyl alcohol, n-butanol, isobutanol, sec-butanol, tert-butanol and cyclohexanol; halogenated hydrocarbon such as methylene chloride, chloroform and chlorobenzene; ketones such as acetone, methyl ethyl ketone and cyclohexanone; esters such as methyl acetate, ethyl acetate, propyl acetate and butyl acetate; ethers such as diethyl ether; amides such as N,N-dimethylformamide and N,N-dimethylacetamide; and dimethylsulfoxide. Particularly preferred are toluene, cyclohexane, methylcyclohexane, methanol and isopropyl alcohol. Also, a combination of these solvents may be used. An appropriate cooling temperature is −20 to 50° C. and preferably −10 to 40° C., though it varies depending on the type and amount of N-vinyl carboxylic acid amide compound and a recrystallizing solvent.

The crystallizer used in the present invention may employ either of a batch mode and a continuous mode, and the crystallizing method may be either of a method by heat exchange with a refrigerant or a method by condensation and cooling owing to evaporation of a solvent, and there are no severe limitations on the structural style. There is no particular limitation either on the crystal separator such as those using vacuum pressure or increased pressure and those using gravity and centrifugal force.

In the present invention, a solid-liquid separator which carries out the crystallizing operation and separation operation in one device can be used. As one such example, pressure crystallization apparatus, falling film crystallization device (MWB fractional crystallizer and the like) and a back mixing column crystallizer (BMC device and the like) are preferable in the case without using a recrystallization solvent. In the case where a slurry at high concentration is filtrated, automatic nutsche filter such as a Rosenmund filter is preferable.

Examples of the usage of the N-vinyl carboxylic acid amide compound obtained by the present invention include use in a reactive diluent, various polymer materials, pharmaceutical materials, agrichemical materials, monomers to improve hygroscopicity through graft polymerization onto the surface of polyester fibers, monomers for surface modification of PET films, solvents and solubilizers.

(ii) Polymerization of the N-Vinyl Carboxylic Acid Amide Compound

A homopolymer of the N-vinyl carboxylic acid amide compound or a copolymer of the N-vinyl carboxylic acid amide compound can be produced by homopolymerization of the N-vinyl carboxylic acid amide compound represented by formula (5)

[Chem. 22]

(5)

(symbols in the formula have the same meanings as mentioned above) or copolymerization of the compound with other monomers which can be copolymerized.

As a polymerization method, a general polymerization method such as polymerization by solution polymerization by allowing the solution to stand still, solution polymerization with stirring, polymerization by dropping a monomer, reversed phase suspension polymerization, emulsion polymerization and precipitation polymerization can be employed. For example, as a solution polymerization method, after dissolving a monomer component and a crosslinking agent uniformly in a solvent such as water, an organic solvent or a mixture thereof; and removing dissolved oxygen in a system by vacuum deaeration or replacement with inert gas such as nitrogen and carbon dioxide; reaction is conducted by the addition of a polymerization initiator. Generally, the polymerization initiation temperature is about −10 to 60° C., and the reaction time is about one to ten hours.

Specific examples of a monomer which is copolymerizable with the N-vinyl carboxylic acid amide compound include the following: acrylic acid, methacrylic acid (hereinafter to be collectively referred to as (meth)acrylic acid) or alkali metal salts thereof such as sodium salts and potassium salts; alkyl ester thereof such as methyl ester, ethyl ester, propyl ester, butyl ester, pentyl ester, hexyl ester, heptyl ester, octyl ester, nonyl ester, decyl ester, hexyldecyl ester and octadecyl ester; hydroxy lower alkyl ester thereof such as hydroxyethyl ester, hydroxypropyl ester and hydroxybutyl ester; lower alkyl ester substituted with lower alkyl amino group thereof such as dimethylaminomethyl ester, dimethylaminoethyl ester, dimethylaminopropyl ester, dimethylaminobutyl ester, diethylaminomethyl ester, diethylaminoethyl ester, diethylaminopropyl ester and diethylaminobutyl ester; lower alkyl ester halide thereof (which halide is preferably chloride or bromide) substituted with quaternary ammonium group such as trimethylammonioethylester halide, trimethylammoniopropylester halide, triethylammonioethylester halide and triethylammoniopropylester halide; amides thereof; lower alkyl amides thereof substituted with lower alkyl amino group such as dimethylaminomethyl amide, dimethylaminoethyl amide, dimethylaminopropyl amide, dimethylaminobutyl amide, diethylaminomethyl amide, diethylaminoethyl amide, diethylaminopropyl amide and diethylaminobutyl amide; lower alkyl amide halide thereof substituted with quaternary ammonium group such as trimethylammonioethylamide halide, trimethylammoniopropylamide halide, triethylammonioethylamide halide and triethylammoniopropylamide halide; lower alkyl amide thereof substituted with sulfonic acid or alkali metal sulfonate such as sulfo methyl amide, sulfo ethyl amide, sulfo propyl amide, sulfo butyl amide, sodium sulfo methyl amide, sodium sulfo ethyl amide, sodium sulfo propyl amide, sodium sulfo butyl amide, potassium sulfo methyl amide, potassium sulfo ethyl amide, potassium sulfo propyl amide and potassium sulfo butyl amide; acrylonitrile; vinyl ether such as methyl vinyl ether, ethyl vinyl ether, propyl vinyl ether and butyl vinyl ether; vinyl ketone such as methyl vinyl ketone and ethyl vinyl ketone; lower carboxylic acid vinyl such as vinyl acetate and vinyl propionate; maleic anhydride, maleic acid, sodium maleate and potassium maleate.

Among these, particularly preferred are (meth)acrylic acid, sodium(meth)acrylate, methyl(meth)acrylate, ethyl(meth)acrylate, propyl(meth)acrylate, butyl(meth)acrylate, (meth)acrylic acid 2-hydroxyethyl ester, (meth)acrylic acid 2-hydroxypropyl ester, (meth)acrylic acid 2-hydroxybutyl ester, (meth)acrylic acid dimethylaminoethyl ester, trimethylaminoethyl(meth)acrylate chloride ester, acrylamide, sulfopropylacrylamide, sulfobutyl acrylamide, sodium sulfopropyl acrylamide, sodium sulfobutyl acrylamide, acrylonitrile, methyl vinyl ether, ethyl vinyl ether, methyl vinyl ketone, ethyl vinyl ketone, vinyl acetate, N-vinyl-2-pyrrolidone, and maleic anhydride.

As a monomer which is copolymerizable with an N-vinyl carboxylic acid amide compound, a crosslinkable monomer which is a compound having two or more unsaturated groups in one molecule or a crosslinking agent can be used. As a crosslinkable monomer, known monomers can be used and examples include tetraallyl oxyethane, pentaerythritol tetraallyl ether, pentaerythritol triallyl ether, trimethyrol propane triallyl ether, ethylene glycol diallyl ether, diethylene glycol diallyl ether, triethylene glycol diallyl ether, diallyl ether, polyallyl ether derived from a compound having two or more hydroxyl groups in one molecule such as monosaccharides, disaccharides, polysaccharides and cellulose; polyallyl ester derived from a compound having two or more carboxyl groups in one molecule such as triallyl trimellitate, triallyl citrate, diallyl oxalate, diallyl succinate, diallyl adipate and diallyl maleate; a compound having two or more allyl groups in one molecule such as diallylamine and triallyl isocyanurate; a compound having two or more vinyl-ester groups in one molecule such as divinyl oxalate, divinyl malonate, divinyl succinate, divinyl glutarate, divinyl adipate, divinyl maleate, divinyl fumarate and trivinyl citrate; bis(N-vinyl carboxylic acid amide) compounds such as N,N'-butylene bis(N-vinylacetamide) and N,N'-diacetyl-N,N'-divinyl-1,4-bisaminomethyl cyclohexane; compounds having multiple acrylamide structures and (meth)acrylate groups such as N,N'-methylenebisacrylamide, ethylene glycol di(meth)acrylate, diethylene glycol di(meth)acrylate, polyethylene glycol di(meth)acrylate, trimethylol propane tri(meth)acrylate and pentaerythritol tri(meth)acrylate; divinyl benzene; divinyl ether; and allyl(meth)acrylate. One member or two or more members thereof can be used as needed.

The N-vinyl carboxylic acid amide (co)polymer made by polymerizing the N-vinyl carboxylic acid amide compound of the present invention can be produced by the method as follows:

A polymerization reaction is carried out in the presence of a polymerization initiator using an N-vinyl carboxylic acid amide compound as an essential monomer. The polymerization reaction can be carried out in an organic solvent which does not substantially dissolve or dissolves the generated copolymer, in an aqueous solution containing an organic solvent, or in an aqueous solution.

Examples of an organic solvent to be used include ethyl acetate, acetone, methyl ethyl ketone, methyl isobutyl ketone, benzene, toluene, methanol, ethanol and isopropanol.

As a polymerization initiator, one generally used in polymerization reaction can be used with no limitation. Examples include persulfate of sodium, potassium, ammonium and the like; peroxide compounds such as lauroyl peroxide, caproyl peroxide, benzoyl peroxide, hydrogen peroxide, pelargonyl peroxide, cumenehydro peroxide, t-butyl perphthalate, t-butylperbenzoate, t-butyl peroxy pivalate, sodium peracetate and sodium percarbonate; azo compounds such as azobisisobutyronitrile, 2,2'-azobis(2-amidinopropane)dihydrochloride, 2,2'-azobis[2-(2-imidazolin)-2-yl)propane]dihydrochloride, 2,2'-azobis[N-(2-carboxyethyl)-2-methyl propionamide], 2,2'-azobis{2-[N-(2-caboxyethyl)amidino] propane}, dimethyl 2,2'-azobis(2-methylpropionate), 4,4'-azobis(4-cyano valeric acid) and 2,2'-azobis(2-methylpropanoic acid).

Among the above polymerization initiators, azobis isobutyronitrile soluble in an organic solvent and 2,2'-azobis(2-amidinopropane)dihydrochloride soluble in water are used in a preferable embodiment. Although the usage of the polymerization initiator varies depending on the type of the initiator and a polymerization method, it can be appropriately determined so that a polymerization reaction proceeds smoothly and an appropriate mass average molecular weight can be obtained. For example, the polymerization initiator is used in 0.1 to 3 mass of the total amount of monomers.

Generally, it is desirable to carry out the polymerization reaction under an inert atmosphere. Although the polymerization temperature cannot be uniformly defined since it has an affect on the average mass molecular weight of the copolymer to be generated, it is desirable to carry out the reaction at a temperature from about 0 to 100° C. to obtain the polymer having a desired mass average molecular weight.

It is also effective to use a molecular weight modifier so as to control the mass average molecular weight within the range of that of the N-vinyl carboxylic acid amide (co)polymer as a target compound.

Examples of the molecular weight modifier include a mercaptan compound and the like, and specifically, dodecyl mercaptan, t-dodecyl mercaptan, thioacetate or a salt thereof, thioethanol, thioglycerol, other alkyl mercaptans and the like can be used. Examples of the other molecular weight modifier which can be used include halogenated substances; sulfides such as dialkyl xanthogen disulfide and diallyl disulfide; phosphorous compounds such as substituted phosphine; and alkylamine.

The usage of the molecular weight modifier is appropriately selected so that the mass average molecular weight of the copolymer as a target compound falls within the above-mentioned range. Generally, it is desirable to use the molecular weight modifier in 0 to 10 mass % based on the raw material monomer. When the molecular weight modifier exceeding 10 mass % is added, the polymerization reaction fails to proceed sufficiently and residual monomer increases, which tends to generate (co)polymers having a mass average molecular weight less than 1,000. As a specific example, when alkyl mercaptan is used as a molecular weight modifier, the additive amount is preferably 0.5 to 5 mass % based on the raw material monomer.

In the case of emulsion polymerization, various emulsifiers are used in order to carry out the polymerization reaction smoothly and to stabilize the generated emulsion. As an emulsifier, it is desirable to use a combination of an anionic surfactant and a nonionic surfactant, and generally used anionic and nonionic surfactants can be used effectively. Examples of the anionic surfactant include sodium dodecyl sulfate, sodium dodecyl benzenesulfonate, sodium dioctyl sulfosuccinate, sodium polyethylene glycol nonylphenylsulfonate, sodium butylnaphthalene sulfonate and sodium rosinate.

Examples of the nonionic surfactant include polyethylene glycol alkyl ether such as polyethylene glycol dodecyl ether and polypropylene glycol octyl ether; polyethylene glycol alkylphenyl ether such as polyethylene glycol dodecylphenyl ether; and polyethylene glycol ester of a long-chain carboxylic acid.

Upon emulsion polymerization, a polymer compound having emulsification capacity can be used solely or in combination with a surfactant. Examples of the polymer compound having emulsification capacity include nature products such as gum arabic and dextrin; and synthetic substances such as polyvinyl alcohol, polyacryl amide, poly-N-vinylacetamide, poly-N-methyl-N-vinylacetamide, poly-N-methyl-N-vinylformamide, poly-N-vinylpyrolidone, poly-N-vinylformamide, polyacrylic acid, polymethacrylic acid, hydroxyethylcellulose; and water-soluble polymers as copolymers of acrylic acid ester or methacrylic acid ester with acrylamide, acrylic acid, methacrylic acid, crotonic acid and the like can also be used. Block copolymers with ethylene oxide and propylene oxide can be used as well.

Examples of the usage of the N-vinyl carboxylic acid amide (co)polymer made by polymerizing the N-vinyl carboxylic acid amide compound of the present invention include adhesives, sand core binders, rubber-metal adhesives, binders for products sintered at high temperature such as clay, ceramics, porcelains and brick articles, dispersing agents for slurry containing ceramics in a medium, viscosity modifiers of ceramics, binders of glass and glass fiber, lubricants and coating agents, ink for ballpoint pens, protective colloid and leveling agents for printing ink, pigment dispersing agents, wax and polish, hair styling products, shampoos, hair dye, cream, shaving and after-shaving products, makeup, deodorants, bath salts, lipsticks, body-care products, skin-care products, toothpastes, flavor binders, coatings/binders of enzymes for the purpose of preventing powder enzymes from scattering, foam stabilizers, agents for suppressing skin irritation, dye transfer inhibiting agents, liquid/powder laundry products, encapsulating agents for detergents, resist additives, aids for ink-jet printing, antistatic agents, sheet soaps, waterless hand cleaners, industrial microbicides, automatic cleaning fluid, grease cleaners, stain removers, suds stabilizers for bubble bath, antifoulants for synthetic fibers and resin processed fibers, binders for tablet personal computer products, battery, printed circuits, acid corrosion inhibitors, brighteners in zinc plating, epoxy resin curing agents, chemical anchor adhesives, metal chelating agents, shadow masks and protection of photo sensitive materials for television cathode-ray tubes, binders for metal salts or amalgam of batteries, compatible dispersing agents for condensation heat transfer fluid such as a plating bath of gold, nickel, copper or zinc and cathode ray tubes, sealants for electrolyte leakage protection inside the battery, expanders for cadmium electrodes, aldehyde absorbents, binders for sintered nickel powder plates, deep etching inhibitors of metal plating, preservative solutions for printing plates, edge coatings, dye fixatives, vehicles, thickeners for fabric finishes and printing ink for various fibers, dye removers upon washing printed products, dye solubilizers; dyeing and printing fibers; dye removing and dispersing agents; fiber delustering agent; grease-resistant adjuncts from fibers, anti-soil-redeposition agents for fibers; dispersing agents of titanium dioxide, dispersing agents of zinc dioxide; various functional membranes such as macroporous membranes, porous membranes, desalination membranes, gas separation membranes, ultrafiltration membranes, blood dialysis membranes, membranes as a material for dew condensation prevention and for substrates for electrode pads for living body, and membranes having selective permeability; anticorrosion agents for the oil quenching bath in metallurgy; mold and core binders; thickeners; viscosity modifiers; adhesion enhancers; water-soluble flux; adhesives; mortar additives; agents for improving strength and stability of paper; dye solubilizers in the steps of improving gloss, binding between the paper fibers, absorbability, whiteness and the like of the paper and the steps of dyeing and decoloring paper; dispersing agents of fibers and pigments in paper production; pitch deposit inhibitors in paper production; substrates for adhesive dermal patches; complex agents with modified resins; inorganic flake and fiber binders in paper production; particle-size controlling agents for emulsion polymers; suspension agents; viscosity modifiers; agents for improving strength, transparency and colorability of polymers; electrophoresis gel; substrates for DDS (drug delivery system); staining capacity improvers for latex; latex stabilizers; scale inhibitors; anticorrosion agents in a water transmission system; scale inhibitors and anti-clogging agents in reverse osmosis membranes and water treatment of fish hatcheries; functional catheters; blood bags; matrixes for regenerative medicines; wound dressings; ophthalmologic materials; medical adhesives; dietary additives; water-soluble films; seamless capsules; binding aids for casting molds; oil/dye remover from drainage water; oil ball coalescing agents in cleaning oil spill; auxiliary agents for boring; coagulant in the drainage treatment; deodorants by neutralization and irritation relieving agents against toxic gas; concrete retarders; sealant property improving agents for boring and casing; viscosity modifiers in marsh mining; disposable diapers; sanitary napkins; wound dressings; incontinence pads; absorption improving agents for various paper and fiber products such as sheets for absorbing blood and the like; agricultural and horticultural water retention agents; food freshness preservatives; sheets for absorbing the drip used for food and distribution; substrates for air fresheners; antifouling bottom paints; dew condensation preventing agents; sealing materials; concrete curing/modifying agents; sandbags filled with water-absorbing gel; transparent gel for observing boreholes; water retaining agents used for a demolition method using a demolition agent filled with gel or a method for greening steep ground; water retaining agents used for a foam shield driving method; luminescent materials for road signs on snowy roads; artificial snow; sustained-release formulations floating in the stomach; mucosal application formulations; antithrombogenic materials; artificial joints; artificial skin; finger coating agents; packaging materials for food freshness preservation; contact dehydrating sheets; double-bottomed instant noodle containers; food containers incorporating an exothermic agent; water sensors; shielding materials for electric cables; medical electrodes; earth for communication; antifouling bottom paints; oil-water separators; old-wall peeling agents; wound balls; vibration dampeners; toys; shock-absorbing materials; actuators; variable-focus-length lenses; and artificial muscles; but the usage is not limited thereto.

EXAMPLES

Hereinafter, the present invention will be explained in more detail below with reference to Examples, but the present invention is not limited thereto unless the objects and advantages of the invention are impaired.

Various measurements were carried out as follows:
H-NMR, $^{13}$C-NMR:
$^1$H-NMR and $^{13}$C-NMR were measured by dissolving the samples in deuterated chloroform using JEOL EX-400 ($^1$H-NMR: 400 MHz, $^{13}$C-NMR: 100 MHz). $^1$H-NMR was measured using tetramethylsilane as an internal standard material to calculate the chemical shift; and the chemical shift of $^{13}$C-NMR was calculated on the assumption that the $^{13}$C chemical shift of CDCl$_3$ is 77.0 ppm.

High-performance liquid chromatography (HPLC):
Pump: DS-4; manufactured by Showa Denko K.K.
Differential reflactometer detector: SE-61; manufactured by Showa Denko K.K.
Ultraviolet absorption detector: UV-41; manufactured by Showa Denko K.K.
Detection wavelength: 215 nm
Used column: Two of Shodex RSpak DE-413L (manufactured by Showa Denko K. K.) were used in tandem.
Eluent: Aqueous solution of NaH$_2$PO$_4$.2H$_2$O (5.69 mmol)+ Na$_2$HPO$_4$.12H$_2$O (14.31 mmol) was used as liquid A.
Acetonitrile: liquid A=5 wt %:95 wt %
Column temperature: 50° C.
Flow rate: 0.8 ml/min.
Measurement conditions of gas chromatograph (GC):
Used column: DB-WAX; manufactured by J&W Scientific Inc.; inner diameter=0.25 mm, film thickness: 0.25 μm
Carrier gas: helium
Flow rate: 1.5 ml/min
Spirit ratio: 1/50
Purge flow rate: 3 ml/min.
Detector: FID
Injection temperature: 200° C.
Detection temperature: 220° C.

Example 1

Figure 1:
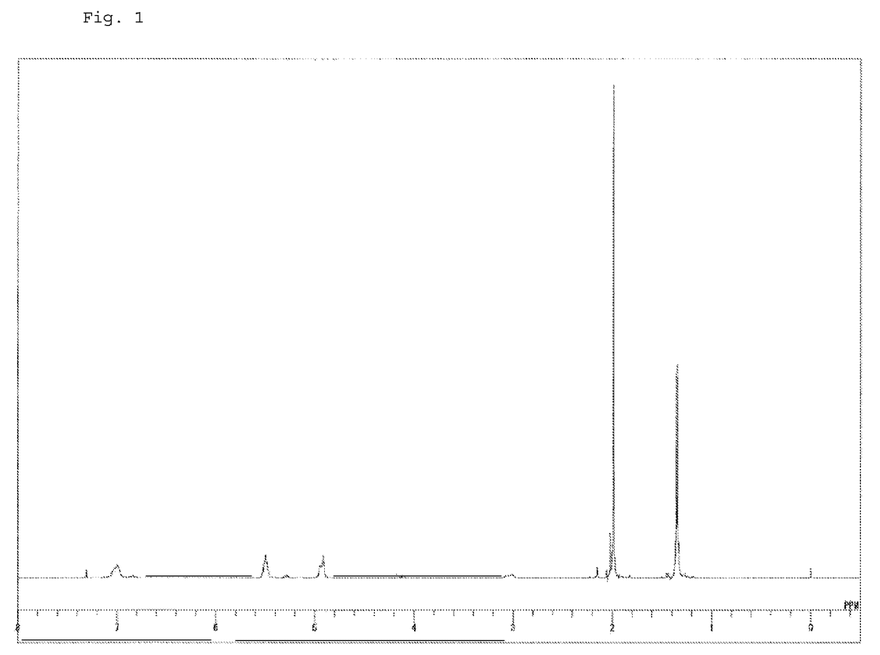
FIG. 1 $^1$H-NMR chart of N-(1-hydroxyethyl)acetamide obtained in Example 1
FIG. 2 $^1$H-NMR chart of N-(1-hydroxyethyl)-N-methylformamide obtained in Example 10

52.57 g of acetamide, 181.65 g (210 ml) of toluene, 47.1 g (60 ml) of acetaldehyde and 277 mg of potassium hydrogen carbonate were charged in a 500 ml-volume glass flask provided with a Dimroth condenser; and the mixture was heated while stirring under nitrogen atmosphere at 40° C. for six hours with pouring cooling water at −10° C. into the Dimroth condenser. From the reaction solution separated into two layers, the lower layer was condensed with an evaporator, and then unreacted acetamide was precipitated as colorless and transparent crystals. The crystals were filtrated to obtain a pale-yellow oily substance (63 g) as a crude product. By measuring $^1$H-NMR of the substance, the substance was found to be a mixture of N-(1-hydroxyethyl)acetamide (42 mol %) as a target compound and acetamide (58 mol %).

Subsequently, column cleanup was developed. Silica gel (manufactured by Wako Pure Chemical Industries, Ltd.; WAKO-GEL C-200) made into slurry by using ethyl acetate was filled into a column chromatographic tube. A part of the crude product obtained in the above step was placed on the upper part of the column chromatographic tube and eluted with ethyl acetate, and fractions showing the Rf value of 0.5 (developing solvent: ethyl acetate) in TLC (manufactured by MERCK Ltd.; Pre-coated TLC Plates SILICA GEL 60 F-254) were collected and condensed under reduced pressure using an evaporator to obtain white solid. The $^1$H-NMR and $^{13}$C-NMR of the solid were measured and it was confirmed that the solid was N-(1-hydroxyethyl)acetamide represented by structure formula (1).

[Chem. 23]

Structure Formula (1)

$^1$H-NMR: δ (ppm) 7.19 (br.s, 1H, NH), 5.51~5.45 (m, 1H, CH), 5.40 (br.s, 1H, OH), 1.97 (s, 3H, $\overline{CH_3}$C(=O)—NH—), 1.34 (d, 3H, J=5.9 Hz, CH$_3$CH(OH)—N$\overline{H}$—).

$^{13}$C{$^1$H}-NMR: δ (ppm) 171.1 (C=O), 70.7 (CH—OH), 23.1 ($\underline{CH_3}$C=O or $\underline{CH_3}$CHOH), 21.4 ($\underline{CH_3}$C=O or $\underline{CH_3}$CHOH)

Example 2

22.3 g of acetamide, 16.9 g of methanol and 1.776 g of potassium hydrogen carbonate were charged under nitrogen atmosphere into a 100 ml-volume glass flask provided with a thermometer, a dropping funnel and a Dimroth condenser with pouring cooling water at −10° C. into the Dimroth condenser. While keeping the reaction temperature of 20° C. or less, 21.20 g of acetaldehyde was delivered by drops and the mixture was stirred under nitrogen atmosphere at room temperature. The reaction solution was condensed by an evaporator and unreacted acetamide was precipitated as colorless and transparent crystals. The crystals were filtrated to obtain pale yellow oily substance as a crude product. The oily substance was measured by high performance liquid chromatography and found out to have acetamide conversion of 57.0% and selectivity to N-(1-hydroxyethyl)acetamide as a target compound of 95%.

Example 3

10.3 g of acetamide, 4.68 g of tetrahydrofurane and 0.17 g of potassium hydrogen carbonate were charged under nitrogen atmosphere into a 100 ml-volume glass flask provided with a thermometer, a dropping funnel and a Dimroth condenser with pouring cooling water at −10° C. into the Dimroth condenser. While keeping the reaction temperature of 20° C. or less, 8.32 g of acetaldehyde was delivered by drops and the mixture was stirred under nitrogen atmosphere at room temperature. The reaction solution was condensed by an evaporator and unreacted acetamide was precipitated as colorless and transparent crystals. The crystals were filtrated to obtain pale yellow oily substance as a crude product. The oily substance was measured by high performance liquid chromatography and found out to have acetamide conversion of 84.8% and selectivity to N-(1-hydroxyethyl)acetamide as a target compound of 96%.

Example 4

10.2 g of acetamide, 29.9 g of the pale yellow oily substance obtained in Example 2 (mixture of N-(1-hydroxyethyl)acetamide and acetamide) and 0.248 g of potassium hydrogen carbonate were charged under nitrogen atmosphere into a 100 ml-volume glass flask provided with a thermometer, a dropping funnel and a Dimroth condenser with pouring cooling water at −10° C. into the Dimroth condenser. While keeping the reaction temperature of 20° C. or less, 17.66 g of acetaldehyde was delivered by drops and the mixture was stirred under nitrogen atmosphere at room temperature for 4.6 hours. The reaction solution was condensed by an evaporator and unreacted acetamide was precipitated as colorless and transparent crystals. The crystals were filtrated to obtain pale yellow oily substance as a crude product. The oily substance was measured by high performance liquid chromatography and found out to have acetamide conversion of 62.9% and selectivity to N-(1-hydroxyethyl)acetamide as a target compound of 97%.

Example 5

20.07 g of acetamide, 22.07 g of methanol and 0.446 g of potassium hydrogen carbonate were charged under nitrogen atmosphere into a 100 ml-volume glass flask provided with a thermometer, a dropping funnel and a Dimroth condenser with pouring cooling water at −10° C. into the Dimroth condenser. While keeping the reaction temperature of 20° C. or less, 21.20 g of acetaldehyde was delivered by drops and the mixture was stirred under nitrogen atmosphere at room temperature. The reaction solution was condensed by an evaporator and unreacted acetamide was precipitated as colorless and transparent crystals. The crystals were filtrated to obtain pale yellow oily substance as a crude product. The oily substance was measured by high performance liquid chromatography and found out to have acetamide conversion of 48.0% and selectivity to N-(1-hydroxyethyl)acetamide as a target compound of 94%.

Example 6

19.38 g of acetamide, 52.25 g of methylcyclohexane, 0.554 g of potassium hydrogen carbonate and 1.24 g of the pale yellow oily substance obtained in Example 2 (mixture of N-(1-hydroxyethyl)acetamide and acetamide) were charged under nitrogen atmosphere into a 100 ml-volume glass flask provided with a thermometer, a dropping funnel and a Dimroth condenser with pouring cooling water at −10° C. into the Dimroth condenser. While keeping the reaction temperature of 20° C. or less, 20.52 g of acetaldehyde was delivered by drops and the mixture was stirred under nitrogen atmosphere at room temperature for one hour. The reaction solution was allowed to stand still and separated into two layers. The lower layer was condensed by an evaporator and unreacted acetamide was precipitated as colorless and transparent crystals. The crystals were filtrated to obtain pale yellow oily substance as a crude product. The oily substance was measured by high performance liquid chromatography (HPLC) and found out to have acetamide conversion of 95.2% and selectivity to N-(1-hydroxyethyl)acetamide as a target compound of 97.5%.

Example 7

20.07 g of acetamide, 39.13 g of tetrahydrofurane and 0.563 g of potassium carbonate were charged under nitrogen atmosphere into a 100 ml-volume glass flask provided with a thermometer, a dropping funnel and a Dimroth condenser with pouring cooling water at −10° C. into the Dimroth condenser. While keeping the reaction temperature of 20° C. or less, 21.20 g of acetaldehyde was delivered by drops and the mixture was stirred under nitrogen atmosphere at room temperature. The reaction solution was condensed by an evaporator and unreacted acetamide was precipitated as colorless and transparent crystals. The crystals were filtrated to obtain pale yellow oily substance as a crude product. The oily substance was measured by high performance liquid chromatography and found out to have acetamide conversion of 65.0% and selectivity to N-(1-hydroxyethyl)acetamide as a target compound of 93%.

Example 8

20.33 g of acetamide, 25.05 g of methanol and 1.8 g of sodium carbonate were charged under nitrogen atmosphere into a 100 ml-volume glass flask provided with a thermometer, a dropping funnel and a Dimroth condenser with pouring cooling water at −10° C. into the Dimroth condenser. While keeping the reaction temperature of 20° C. or less, 18.29 g of acetaldehyde was delivered by drops and the mixture was stirred under nitrogen atmosphere at room temperature. The reaction solution was condensed by an evaporator and unreacted acetamide was precipitated as colorless and transparent crystals. The crystals were filtrated to obtain pale yellow oily substance as a crude product. The oily substance was measured by high performance liquid chromatography and found out to have acetamide conversion of 44.4% and selectivity to N-(1-hydroxyethyl)acetamide as a target compound of 95%.

Example 9

19.78 g of N-methylacetamide, 21.22 g of methylcyclohexane, 380 mg of potassium carbonate were charged under nitrogen atmosphere into a 100 ml-volume glass flask provided with a thermometer, a dropping funnel and a Dimroth condenser with pouring cooling water at −10° C. into the Dimroth condenser. While keeping the reaction temperature of 20° C. or less, 19 ml of acetaldehyde was delivered by drops for 13 minutes and the mixture was stirred under nitrogen atmosphere at room temperature. The reaction solution was allowed to stand still and separated into two layers. The lower layer was condensed by an evaporator and unreacted acetamide was precipitated as colorless and transparent crystals. The crystals were filtrated to obtain pale yellow oily substance as a crude product. The oily substance was measured by high performance liquid chromatography and found out to have N-methylacetamide conversion of 20.2% and selectivity to N-(1-hydroxyethyl)-N-methylacetamide as a target compound of 95%.

Example 10

Figure 2:
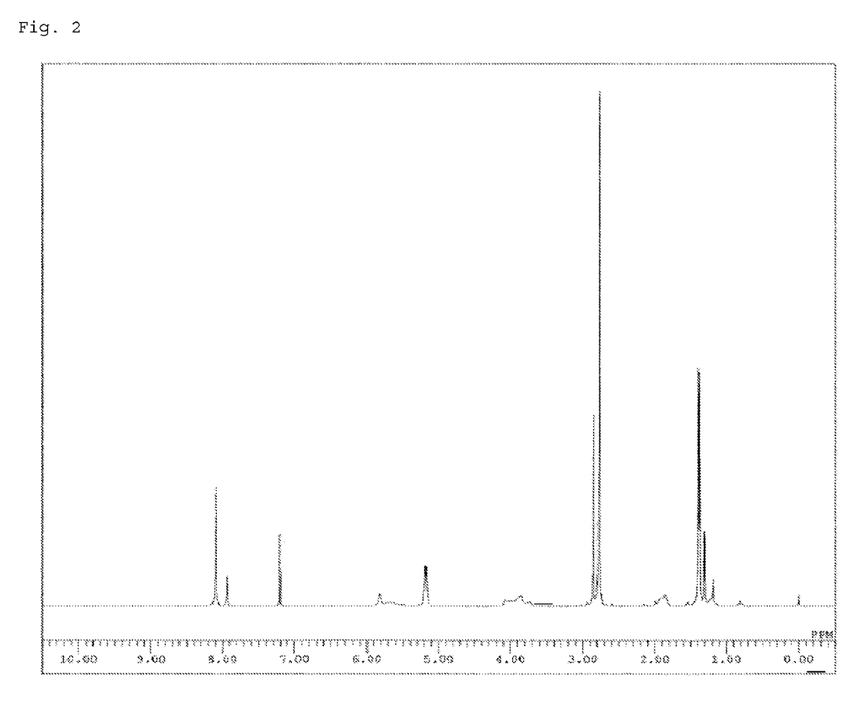

19.78 g of N-methylformamide, 21.22 g of methylcyclohexane, 380 mg of potassium carbonate were charged into a 500 ml-volume glass flask provided with a Dimroth condenser with pouring cooling water at −10° C. into the Dimroth condenser. While keeping the reaction temperature of 20° C. or less, 19 ml of acetaldehyde was delivered by drops and the mixture was stirred under nitrogen atmosphere at room temperature. Among the two separated layers of the reaction solution, the lower layer was measured by high performance liquid chromatography and found out to have N-methylformacetamide conversion of 85% and selectivity to N-(1-hydroxyethyl)-N-methylformamide as a target compound of 97%. Next, the lower layer was condensed by an evaporator to obtain pale yellow oily substance. The column cleanup of the pale yellow oily substance was developed. Silica gel (manufactured by Wako Pure Chemical Industries, Ltd.; WAKO-GEL C-200) made into slurry by using ethyl acetate was filled into a column chromatographic tube. A part of the crude product obtained in the above step was placed on the upper part of the column chromatographic tube and eluted with ethyl acetate, and fractions showing the Rf value of 0.45 (developing solvent: ethyl acetate) in TLC (manufactured by MERCK Ltd.; Pre-coated TLC Plates SILICA GEL 60 F-254) were collected and condensed under reduced pressure using an evaporator to obtain pale yellow oily substance. The $^1$H-NMR of the oily substance was measured and it was confirmed that the substance was N-(1-hydroxyethyl)-N-methylformamide represented by structure formula (2) and N-methylformamide as a raw material.

[Chem. 24]

Structure formula (2)

$^1$H-NMR: δ (ppm) 8.09 (s, 1H, CHO), 5.19-5.18 (m, 1H, CH), 2.78 (s, 3H, —N(CH$_3$)—), 1.38 (d, 3H, J=5.9 Hz, CH$_3$CH(OH)—N(CH$_3$)—)

Example 11

20.34 g of the pale yellow oily substance obtained in Example 6, 22.3 g of methanol and 20 mg of concentrated sulfuric acid were charged under nitrogen atmosphere into a 100 ml-volume glass flask provided with a thermometer and a Dimroth condenser with pouring cooling water at 5° C. into the Dimroth condenser, and the mixture was stirred under nitrogen atmosphere at room temperature for 30 minutes. Next, 0.6 g of 3% sodium hydroxide aqueous solution was added thereto and the precipitated salt was filtrated. The reaction solution was condenced by an evaporator and the obtained condensed solution was purified by distillation under reduced pressure. The fractions having a boiling point from 70 to 100° C. (absolute pressure: 0.3 to 1.3 kPaA) were collected. As a result of the analysis by gas chromatography, the fractions were found to be composed of 5% of acetamide and 950 of N-(1-methoxyethyl)acetamide.

Next, the obtained fraction mainly comprising N-(1-methoxyethyl)acetamide was gasified at 175° C., heated to 440° C. and supplied to a stainless-steel reaction tube evacuated to 100 mmHg. The mixture of N-vinylacetamide and methanol generated by heat decomposition reaction was condensed by a condenser provided at the outlet of the reaction tube and was recovered. The N-(1-methoxyethyl)acetamide conversion was found to be 88%.

Methanol generated by heat decomposition reaction was distilled away from the thus-obtained pyrolysis liquid while increasing the depressurization degree from 10 kPa to 3 kPa. The analysis of the concentrated liquid after the distillation showed that the liquid contained 70 mass % of N-vinylacetamide, 16.1 mass of N-(1-methoxyethyl)acetamide, 11.3 mass of acetamide, 60 mass ppm of N-1,3-butadienylacetamide and 2.6 mass % of the other components. The other components were measured by gas chromatography (GC) and found to contain 40 mass ppm of butanal and 90 mass ppm of hexanal. Next, methanol was added to 5 g of a solid catalyst in which 0.5 mass of paradium was supported on the alumina support and the above-mentioned mixture solution of N-vinylacetamide so that the solution reaches a methanol concentration of 20 mass %. The resultant solution was put in a 100 ml-volume flask and stirred under hydrogen atmosphere at room temperature for 30 minutes to carry out the reaction. After the reaction was completed, the catalyst was filtrated from the reaction solution and the obtained solution was cooled by 1° C. per hour to thereby precipitate part of N-vinylacetamide, and the obtained slurry was subjected to solid-liquid separation by a centrifuge. The analysis of the obtained solid showed that the N-vinylacetamide had a purity of 99.6 wt %.

Example 12

200 g of N-methylacetamide, 300 g of methylcyclohexane and 3.79 g of potassium carbonate were charged under nitrogen atmosphere into a 1 l-volume glass flask provided with a thermometer, a dropping funnel and a Dimroth condenser with pouring cooling water at −10° C. into the Dimroth condenser. While keeping the reaction temperature of 20° C. or less, 144.6 g of acetaldehyde was delivered by drops for two hours and the mixture was stirred under nitrogen atmosphere at room temperature for one day. The reaction solution was allowed to stand still and separated into two layers. The lower layer was moved to another glass flask and 100 g of methanol containing 1,000 ppm of concentrated sulfuric acid was added thereto and the mixture was stirred at room temperature for three hours.

Next, 0.6 g of 3% sodium hydroxide aqueous solution was added thereto and the precipitated salt was filtrated. The reaction solution was condensed by an evaporator and the obtained concentrated liquid was purified by distillation under reduced pressure. The fractions having a boiling point from 50 to 80° C. (absolute pressure: 0.3 to 1.3 kPaA) were collected. As a result of the analysis by gas chromatography, the fractions were found to be composed of 12% of N-methyl acetamide and 88% of N-(1-methoxyethyl)-N-methylacetamide.

Next, the obtained fraction mainly comprising N-(1-methoxyethyl)-N-methylacetamide was gasified at 170° C., heated to 440° C. and supplied to a stainless-steel reaction tube evacuated to 100 mmHg. The mixture of N-methyl-vinylacetamide and methanol generated by heat decomposition reaction was condensed by a condenser provided at the outlet of the reaction tube and was recovered. The N-(1-methoxyethyl) acetamide conversion was found to be 89%.

Methanol generated by heat decomposition reaction was distilled away from the thus-obtained pyrolysis liquid while increasing the depressurization degree from 10 kPa to 3 kPa. The analysis of the concentrated liquid after the distillation showed that the liquid contained 73 mass % of N-methyl-N-vinylacetamide, 15.1 mass % of N-(1-methoxyethyl)-N-methylacetamide, 10.9 mass % of N-methylacetamide, 450 mass ppm of N-1,3-butadienyl-N-methylacetamide and 1 mass % of the other components. The other components were measured by gas chromatography (GC) and found to contain 240 mass ppm of butanal and 100 mass ppm of hexanal. Next, 2.5 kg of a solid catalyst in which 0.5 wt % of paradium was supported on the alumina support was filled in the hydrogenation reactor under nitrogen atmosphere. Methanol was added to the above N-methyl-N-vinylacetamide mixture solution so that the solution reaches a methanol concentration of 20 mass %. The resultant solution was subjected to circulation flow in the reactor at 20° C. and liquid hourly space velocity (LHSV) 60 Hr$^{-1}$ for six hours. The obtained solution was purified by distillation under reduced pressure. The fractions having a boiling point from 70 to 71° C. (absolute pressure: 3.3 kPaA) were collected. The fractions were analyzed by gas chromatography and the N-methyl-N-vinylacetamide was found to have a purity of 99.8 mass %.

Example 13

185 g of N-methylformamide, 250 g of methylcyclohexane and 4.3 g of potassium carbonate were charged under nitrogen atmosphere into a 1 l-volume glass flask provided with a thermometer, a dropping funnel and a Dimroth condenser with pouring cooling water at −10° C. into the Dimroth condenser. While keeping the reaction temperature of 20° C. or less, 165.6 g of acetaldehyde was delivered by drops for three hours and the mixture was stirred under nitrogen atmosphere at room temperature for one day. The reaction solution was allowed to stand still and separated into two layers. The lower layer was moved to another glass flask and 120 g of methanol containing 1,000 ppm of concentrated sulfuric acid was added thereto and the mixture was stirred at room temperature for two hours.

Next, 0.8 g of 3% sodium hydroxide aqueous solution was added thereto and the precipitated salt was filtrated. The reaction solution was condensed by an evaporator and the obtained condensed solution was purified by distillation under reduced pressure. The fractions having a boiling point from 62 to 85° C. (absolute pressure: 0.3 to 1.3 kPaA) were collected. The fractions were analyzed by gas chromatography and found to be composed of 9% of N-methylformamide and 88% of N-(1-methoxyethyl)-N-methylformamide.

Next, the obtained fraction mainly comprising N-(1-methoxyethyl)-N-methylformamide was gasified at 170° C., heated to 440° C. and supplied to a stainless-steel reaction tube evacuated to 100 mmHg. The mixture of N-methyl-vinylformamide and methanol generated by heat decomposition reaction was condensed by a condenser provided at the outlet of the reaction tube and was recovered. The N-(1-methoxyethyl)formamide conversion was found to be 90.5%.

Methanol generated by heat decomposition reaction was distilled away from the thus-obtained pyrolysis liquid while increasing the depressurization degree from 10 kPa to 3 kPa. The analysis of the concentrated liquid after the distillation showed that the liquid contained 75 mass % of N-methyl-N-vinylformamide, 13.1 mass % of N-(1-methoxyethyl)-N-methylformamide, 10.5 mass % of N-methylformamide, 500 mass ppm of N-1,3-butadienyl-N-methylformamide and 1.4 mass % of the other components. The other components were measured by gas chromatography (GC) and found to contain 110 mass ppm of butanal and 320 mass ppm of hexanal. Next, 25 g of a solid catalyst in which 0.5 wt % of paradium was supported on the alumina support was filled in the hydrogenation reactor under nitrogen atmosphere. Methanol was added to the above N-methyl-N-vinylformamide mixture solution so that the solution reaches a methanol concentration of 20 mass % to thereby circulate the solution at hydrogen pressure of 6 kg/cm2, liquid hourly space velocity of 3 (1/hour) and a temperature of 20° C. The obtained solution was purified by distillation under reduced pressure. The fractions having a boiling point from 42 to 45° C. (absolute pressure: 1.6 kPaA) were collected. The fractions were analyzed by gas chromatography and the N-methyl-N-vinylformamide was found to have a purity of 99.7 mass %.

Example 14

7.45 g of water, 2.50 g N-vinylacetamide obtained in Example 11 and 4 mg of N,N'-(diacetyl)-N,N'-(divinyl)-1,4-bis(aminomethyl)cyclohexane as a crosslinking agent were put and dissolved in a glass test tube. After removing the dissolved oxygen with nitrogen gas, 0.8 mg of 2,2'-azobis-2-(2-imidazolin-2-yl)propane]dihydrochloride dissolved in 0.05 ml of deaerated water as a polymerization initiator was added and the resultant solution was insulated and allowed to stand still. After seven hours, the temperature inside the reactor reached 71° C. by the heat of polymerization. The obtained hydrous polymer was dried and pulverized to obtain a liquid absorbing agent. The absorption of the obtained liquid absorbing agent of poly-N-vinylacetamide was 31 times according to the BOX method.

Example 15

7.45 g of water and 2.50 g N-vinylacetamide obtained in Example 11 were put and dissolved in a glass test tube. After removing the dissolved oxygen with nitrogen gas, 0.5 mg of 2,2-azobis(2-methyl propionamidine)dihycrochloride dissolved in 0.05 ml of deaerated water as a polymerization initiator was added and the resultant solution was insulated and allowed to stand still. After 6.4 hours, the temperature inside the reactor reached 69° C. by the heat of polymerization. The obtained hydrous polymer was dried and pulverized and classified to obtain a thicknener. The obtained thickener of poly-N-vinylacetamide was made into a 0.2% aqueous solution to measure the viscosity with a rotating viscometer at 20° C. and 30 rpm after 30 minutes, and was found to have a viscosity of 11 mPa·s.

Example 16

90 g of acetone, 9 g of N-vinylacetamide obtained in Example 11, 1 g of methacrylic acid and 0.1 g of pentaerythritol acrylate as a crosslinking agent were put and dissolved in a glass reactor and heated to boiling. 30 mg of cumyl peroxide as an initiator was added and the resultant solution was kept boiling. As the polymerization proceeds, generated polymer was precipitated into acetone. After the solution was allowed to cool, the polymer was subjected to suction filtration, dried in vacuum at 50° C. for 24 hours and crushed to thereby obtain 9.7 g of polymer in the fine powder form. The microgel of the obtained poly-N-vinylacetamide copolymer was made into a 1% aqueous solution to measure the viscosity with a rotating viscometer at 20° C. and 30 rpm after 30 minutes, and was found to have a viscosity of 200 mPa·s.

Example 17

10 g of N-methyl-N-vinylacetamide obtained in Example 12 and 0.1 g of N,N'-(diacetyl)-N,N'-(divinyl)-1,4-bis(aminomethyl)cyclohexane as a crosslinking agent were dissolved in 90 g of ethyl acetate and heated to boiling. 0.2 mg of azobisisobutyronitrile as a radical polymerization initiator was added and the resultant solution was kept boiling. As the polymerization proceeded, generated poly-N-methyl-N-vinylacetamide was precipitated into ethyl acetate and the solution was kept in the state for 3.5 hours. After the solution was allowed to cool, the polymer was subjected to suction filtration, dried in vacuum at 55° C. for 24 hours and crushed to thereby obtain 9.8 g of N-methyl-N-vinylacetamide polymer in the fine powder form. The 1% aqueous solution made of the poly-N-methyl-N-vinylacetamide was measured for the viscosity with a rotating viscometer at 20° C. and 30 rpm after 30 minutes, and was found to have a viscosity of 112 mPa·s.

Example 18

10 g of N-methyl-N-vinylacetamide obtained in Example 12, 90 g of epoxy methacrylate resin EA, 2 g of methyl ethyl ketone peroxide as a heat polymerization initiator (manufactured by NOF Corporation; tradename: Permek N) and 0.4 g of cobalt naphthenate were mixed and dissolved. #450 continuous glass mat was impregnated with the solution, laminated to have a thickness of about 2 mm, coated with Mylar film and allowed to stand at room temperature for one day to be cured. The barcol hardness according to JIS K-6911 (measured using a barcol hardness tester 934-1 type) and flexural strength of the cured molding were measured, and the cured molding exerted sufficient strength (barcol hardness: 40, flexural strength: 111 MPa and flexural modulas: 4.8 GPa).

Example 19

7.5 g of N-methyl-N-vinylformamide obtained in Example 13, 5.25 g of methacrylic acid(2-hydroxyethyl), 1.5 g of butyl methacrylate, 0.75 g of acrylic acid were dissolved in 45 g of ethanol and put into a 1 l-volume flask provided with a condenser, a thermometer, stirring device and dropping device and the solution was refluxed at about 80° C. under nitrogen stream 0.10 g of dimethyl 2,2'-azobis(2-methylpropionate) as an azobis polymerization initiator was added thereto at once to carry out polymerization. After the addition of the initiator, the solution was refluxed for six hours to complete the polymerization reaction.

The 1% aqueous solution made of the poly-N-methyl-N-vinylformamide copolymer was measured for the viscosity with a rotating viscometer at 20° C. and 30 rpm after 30 minutes, and was found to have a viscosity of 110 mPa·s.

Example 20

10 g of N-methyl-N-vinylformamide obtained in Example 13 was dissolved in 90 g of ethyl acetate. After bubbling nitrogen gas into the solution at 1 l/min. for 30 minutes, the solution was heated to 70° C. After adding 0.2 mg of azobisisobtyronitrile as a radical polymerization initiator, the solution was kept in a state at 70° C. under nitrogen atmosphere. As the polymerization proceeded, the generated polymer was precipitated into ethyl acetate. After the solution was allowed to cool, the polymer was subjected to suction filtration, dried in vacuum at 55° C. for 24 hours and crushed to thereby obtain 9.8 g of poly-N-methyl-N-vinylformamide in the fine powder form. The 1% aqueous solution made of the poly-N-methyl-N-vinylformamide was measured for the viscosity with a rotating viscometer at 20° C. and 30 rpm after 30 minutes, and was found to have a viscosity of 90 mPa·s.

The invention claimed is:

1. A method for producing an N-(1-hydroxyethyl)carboxamide compound represented by formula (1)

(1)

(wherein $R^A$ and $R^B$ are independently selected from the group consisting of a hydrogen atom, methyl group, ethyl group, n-propyl group, i-propyl group, n-butyl group, i-butyl group, s-butyl group and t-butyl group, provided that $R^A$ and $R^B$ cannot simultaneously be a hydrogen atom), comprising adding N-(1-hydroxyethyl)carboxamide compound as a target compound to a reaction solvent comprising methylcyclohexane, and reacting acetaldehyde and carboxylic acid amide represented by formula (2)

(2)

(wherein $R^A$ and $R^B$ are independently selected from the group consisting of a hydrogen atom, methyl group, ethyl group, n-propyl group, i-propyl group, n-butyl group, i-butyl group, s-butyl group and t-butyl group, provided that $R^A$ and $R^B$ cannot simultaneously be a hydrogen atom) in the presence of a base, the solvent and the N-(1-hydroxyethyl)carboxamide compound.

2. The method for producing the N-(1-hydroxyethyl)carboxamide compound as claimed in claim 1, wherein the base is bicarbonate.

\* \* \* \* \*